United States Patent
Freimann (10) Patent No.: US 8,822,942 B2
(45) Date of Patent: Sep. 2, 2014

(54) PROJECTION EXPOSURE TOOL FOR MICROLITHOGRAPHY WITH A RADIATION DETECTOR DETECTING RADIATION WITH HIGH RESOLUTION OVER A TWO-DIMENSIONAL AREA

(71) Applicant: Carl Zeiss SMT GmbH, Oberkochen (DE)

(72) Inventor: Rolf Freimann, Aalen (DE)

(73) Assignee: Carl Zeiss SMT GmbH, Oberkochen (DE)

( * ) Notice: Subject to any disclaimer, the term of this patent is extended or adjusted under 35 U.S.C. 154(b) by 0 days.

(21) Appl. No.: 13/973,078

(22) Filed: Aug. 22, 2013

(65) Prior Publication Data

US 2013/0334426 A1    Dec. 19, 2013

Related U.S. Application Data

(63) Continuation of application No. 13/719,021, filed on Dec. 18, 2012, now Pat. No. 8,541,752, which is a continuation of application No. PCT/EP2011/002933, filed on Jun. 15, 2011.

(30) Foreign Application Priority Data

Jun. 18, 2010 (DE) .......................... 10 2010 030 261

(51) Int. Cl.
*G01J 1/24* (2006.01)
*G03F 7/00* (2006.01)

(52) U.S. Cl.
USPC ........................................................ 250/372

(58) Field of Classification Search
USPC .......... 250/365, 370.08, 370.09, 372, 492.22; 355/67

See application file for complete search history.

(56) References Cited

U.S. PATENT DOCUMENTS

2006/0264016 A1  11/2006  Hyde et al.
2006/0269117 A1  11/2006  Seitz et al.

(Continued)

FOREIGN PATENT DOCUMENTS

DE    10318562 A1    11/2004
DE    103 32 059 A1   1/2005

(Continued)

OTHER PUBLICATIONS

Linincott-Schwartz, J., et al. "Putting super-resolution fluorescence microscopy to work", Nature Methods, vol. 6, No. 1, Jan. 2009, pp. 21-23, published online Dec. 17, 2008.

(Continued)

*Primary Examiner* — Mark R Gaworecki
(74) *Attorney, Agent, or Firm* — Edell, Shapiro & Finnan LLC (57) ABSTRACT

A method for locally resolved measurement of a radiation distribution (24) produced using a lithography mask (16) comprises providing a radiation converter (31, 131) having an at least two-dimensional arrangement of converter elements (32, 132) which can respectively be put in an active and a passive state, and are configured to convert incoming radiation in respect of its wavelength in the active state. The method further includes: manipulating the radiation converter (31, 131) several times such that respectively only a fraction of the converter elements (32, 132) adopts the active state, irradiating the radiation converter (31, 131) with the radiation distribution (24) after every manipulation of the radiation converter (31, 131) so that the active converter elements (32, 132) emit wavelength-converted is measuring radiation (34), recording respective places of origin (54) of the measuring radiation at every irradiation with the radiation distribution (24).

17 Claims, 5 Drawing Sheets

(56) References Cited

U.S. PATENT DOCUMENTS

2008/0128643 A1 6/2008 Mueller et al.
2009/0134342 A1 5/2009 Hell et al.

FOREIGN PATENT DOCUMENTS

| DE | 10 2009 005 230 A1 | 9/2009 |
|---|---|---|
| WO | 03/058344 A2 | 7/2003 |
| WO | 2006089724 A1 | 8/2006 |
| WO | 2006127692 A2 | 11/2006 |
| WO | 2008091296 A2 | 7/2008 |
| WO | 2009003948 A2 | 1/2009 |

OTHER PUBLICATIONS

Bates, M. et al., "Super-resolution microscopy by nanoscale localization of photo-switchable fluorescent probes", Current Opinion in Chemical Biology 2008, pp. 505-514, published online Sep. 19, 2008.
"Phosphor Screens", Proxitronic Detector Systems Manual.
M. Bossi, et al., "Multicolor Far-Field Fluorescence Nanoscopy through isolated Detection of Distinct Molecular Species", Nano Letters 2008, vol. 8, No. 8, pp. 2463-2468, published Jul. 22, 2008.
Booth, M., et al., "High-resolution EUV imaging tools for resist exposure and aerial image monitoring", Proc. SPIE, vol. 5751, 2005, S. 78-89.
M. Heilemann, et al., "Super-resolution imaging with small organic fluorophores", Angewandte Chemie International Edition, vol. 48, Issue 37, pp. 6903-6908. 2009.
M. Bates, et al., "Multicolor Super-Resolution Imaging with Photo-Switchable Fluorescent Probes", Science 2007, 317: pp. 1749-1759, published Aug. 16, 2007.
German Office Action for German counterpart Patent Application No. 10 2010 0320 261.9-51, dated Feb. 4, 2011.
International Search Report and Written Opinion for counterpart International Patent Application No. PCT/EP/2011/002933, dated Aug. 11, 2011.

PROJECTION EXPOSURE TOOL FOR MICROLITHOGRAPHY WITH A RADIATION DETECTOR DETECTING RADIATION WITH HIGH RESOLUTION OVER A TWO-DIMENSIONAL AREA

This is a Continuation of U.S. application Ser. No. 13/719,021, filed on Dec. 18, 2012, which is a Continuation of International Application PCT/EP2011/002933, with an international filing date of Jun. 15, 2011, and which claims priority to German Patent Application No. 10 2010 030 261.9 filed Jun. 18, 2010. The entire disclosures of these parent patent applications are incorporated into the present continuation by reference.

FIELD OF AND BACKGROUND TO THE INVENTION

The invention relates to a method for the locally resolved measurement of a is radiation distribution produced using a lithography mask, e.g. within the framework of a projection exposure tool or a mask inspection device, an apparatus for the locally resolved measurement of a radiation distribution, a projection exposure tool for microlithography, and a mask inspection device for inspecting a lithography mask.

In order to measure optical systems in microlithography in respect of their imaging quality, one often resorts to the so-called aerial image measuring technique. The aerial image measuring technique is in contrast to a structure-producing measuring technique, wherein a measuring structure is imaged onto a photoresist layer of a wafer and the photoresist structure thus produced is then measured. With the aerial image measuring technique an aerial image sensor is used with which the intensity distribution of an imaged measuring object structure is detected, locally resolved, in the three-dimensional space in at least two directions, for example two lateral directions in relation to the optical axis of the imaging optics used. The measurement of the intensity distribution must not necessarily take place in air here, but it can also be implemented in a different gaseous or liquid medium or in a vacuum.

With the conventional aerial image measuring technique a basic distinction is made between imaging techniques and scanning techniques. With scanning techniques an aerial image sensor is moved mechanically within the three-dimensional space and detects the radiation intensities point by point at the corresponding points of the space. The aerial image sensor only measures one signal value here at the respective time. The measurement of an at least two-dimensional radiation distribution is therefore very time-consuming with this method.

In order to reduce the measuring time, radiation detectors with which electromagnetic radiation can be detected, locally resolved, are therefore often used. US 2006/0269117A1 thus discloses an aerial image detector for radiation in the extreme ultraviolet wavelength range (EUV) which generates an optical is object in the visible light range from the EUV aerial image by using a scintillator. This is imaged, enlarged, onto a camera by high-aperture imaging optics. The resolution limit for these types of imaging objective is a function of the wavelength of the light used for the imaging in the far field, and with visible light is over 100 nm. This resolution is not high enough, however, for the qualification of modern EUV projection objectives or EUV lithography masks.

Furthermore, it is possible to introduce into the aerial image a solid body which emits photoelectrons and to detect the latter, spatially resolved, with an electron microscope, as described in WO 03/058344A2. However, this method requires a very high level of complexity.

OBJECTS AND SUMMARY

It is an object of the invention to provide a method and an apparatus for the locally resolved measurement of a radiation distribution with which the aforementioned problems can be resolved, and in particular the radiation distribution can be measured at least two-dimensionally with a high resolution with justifiable expenditure of time.

The aforementioned object is achieved according to one formulation of the invention with a method for the locally resolved measurement of a radiation distribution produced using a lithography mask. A lithography mask can be in the form of a product mask or also of a test mask. Within the context of the application, a mask is understood to be both a (conventional) solid mask and a variable mask, which comprises e.g. spatial light modulators. The radiation distribution is produced in particular by projection optics downstream of the lithography mask. The method includes: providing a radiation converter with an at least two-dimensional arrangement of converter elements which can respectively be put in an active and a passive state, and are configured to convert incoming radiation with respect to its wavelength in the active state, and manipulating the is radiation converter several times such that respectively only a fraction of the converter elements adopts the active state, irradiating the radiation converter with the radiation distribution after every manipulation of the radiation converter so that the active converter elements emit wavelength-converted measuring radiation, and recording respective places of origin of the measuring radiation at every irradiation with the radiation distribution. Furthermore, according to the method, the radiation distribution produced by the lithography mask is determined from the places of origin recorded with the different irradiation steps.

In other words, according to this aspect of the invention a method for the locally resolved measurement of an aerial image produced using a lithography mask within the framework of a projection exposure tool or a mask inspection device is provided. The aerial image to be measured can for example be the radiation distribution in the wafer plane of a projection exposure tool for lithography or the radiation distribution which is present in the detector plane when inspecting a lithography mask in a mask inspection device.

According to this aspect of the invention, a radiation converter is provided which has an at least two-dimensional arrangement of converter elements. The converter elements can respectively be put in an active and a passive state, and they convert incoming radiation, in particular the radiation of the radiation distribution produced by the lithography mask, into wavelength-converted radiation in the active state. The wavelength of the radiation distribution can be, for example, in the DUV wavelength range, and in particular 193 nm, or in the EUV wavelength range. Photoactivatable fluorescence dyes, for example, can be used as converter elements, as will be described in greater detail below.

According to this aspect of the invention, the radiation converter is manipulated such that only a fraction of the converter elements is put in the active state. Depending on the embodiment, this fraction is smaller than a tenth, smaller than a hundredth and in particular smaller than a thousandth of the converter elements is present overall. After this the radiation converter is subjected to the radiation distribution so that the converter elements in the active state emit the wavelength-converted radiation in the form of measuring radiation. The wavelength of the measuring radiation is preferably longer than the irradiated radiation and can be, for example, in the visible wavelength range.

The places of origin of the measuring radiation are then determined with a high degree of accuracy. For this purpose the plane of the radiation converter is preferably imaged with enlarging imaging optics onto a locally resolving radiation detector, for example a CCD camera. Since only a small fraction of the converter elements has been activated and emits the measuring radiation, according to statistical expectations the Airy discs of the places of origin to be measured do not overlap on the detector. It is therefore possible to determine the places of origin with greatly increased measuring accuracy in comparison to the extension of the Airy discs.

Then the aforementioned steps of manipulating the radiation converter in order to put a fraction of the converter elements in the active state of the radiation converter and of recording the places of origin of the measuring radiation which is then emitted is repeated several times, the converter elements respectively put in the active state being selected according to the principle of statistical chance so that after having passed through a sufficient number of times the predominant majority of the converter elements is present at least once in the active state. According to the invention, from all of the recorded places of origin the radiation distribution produced by the lithography mask is finally determined.

The fundamental principle being applied here of achieving a resolution passing beyond the resolution limit limited by diffraction by irradiating several times respectively different groups of converter elements that are in the active state, is known from cell microscopy. In connection with this one speaks of super-resolving cell microscopy, as for example in the article "Super-resolution microscopy by nanoscale localization of photo-switchable fluorescent probes" by is Mark Bates, et al., Current Opinion in Chemical Biology 2008, 12: 505-514. In super-resolving cell microscopy an aerial image, as with the present invention, is not measured, however, but rather a spatially different distribution of photoactivatable fluorescence molecules in a cell biological sample.

By applying, according to this aspect of the invention, the fundamental principle known from cell biology to aerial image measurement in lithography it is possible to come considerably below the resolution limit preset by diffraction optics in aerial image measurement, and so to enable, particularly for very small wavelengths, for example 193 nm or EUV wavelengths, sufficiently high resolution accuracies in aerial image measurement. At the same time, however, the method according to the invention constitutes an at least two-dimensionally parallel measuring measurement method, and so the time required to measure the radiation distribution is small, at least compared with scanning measuring methods.

In one embodiment according to the invention the converter elements are photoactivatable and the manipulation of the radiation converter is implemented by irradiating an activation radiation of such an intensity that only a fraction of the converter elements adopts the active state. Examples of these photoactivatable converter elements are the photoactivatable fluorescence molecules already mentioned above.

In one embodiment according to the invention the radiation distribution is produced by imaging the lithography mask using a projection exposure tool for microlithography. The radiation distribution to be measured is preferably the radiation present in the wafer plane of the projection exposure tool—the so-called aerial image.

In a further embodiment according to the invention the radiation distribution is produced by imaging the lithography mask using a mask inspection device. These types of mask inspection device are used in order to qualify lithography masks.

In a further embodiment according to the invention the irradiation of the radiation distribution is interrupted in order to irradiate the activation radiation onto the radiation converter. This can be implemented, for example, with a switchable radiation source or a moveable aperture.

In a further embodiment according to the invention, after irradiating the radiation distribution the converter elements are put in the passive state or are deactivated. According to one embodiment this can be implemented by irradiating with high-intensity exposure radiation over the whole surface. It is thus ensured that when the next activation and irradiation passes through, converter elements from the previous measuring passage will not still be active.

In a further embodiment according to the invention the converter elements are configured such that directly after emitting the wavelength-converted measuring radiation they pass temporarily into the passive state in which the converter elements do not convert incoming radiation in respect of their wavelength. Manipulation of the radiation converter is implemented by the radiation converter initially being irradiated with radiation of such an intensity that substantially all of the converter elements are stimulated to emit the wavelength-converted measuring radiation, and are thus temporarily put in the passive state. The radiation distribution is irradiated onto the radiation converter at a time when only a fraction of the converter elements has returned to the active state. When using fluorescence material the passive state can be a temporary non-fluorescent state from which the fluorescence elements fall back into the fluorescent state with a statistical probability. In other words, after the measuring radiation is emitted a "dead time" occurs during which the converter element can not be stimulated to emit the measuring radiation. Substances which are considered as converter elements for this embodiment include e.g. Alexa Fluor 488, ATTO520, Alexa Fluor 532, ATTO532, ATTO565, Alexa Fluor 568, ATTO655 and ATTO700.

According to the embodiment according to the invention the converter elements is are initially irradiated such that substantially all of the converter elements are stimulated to emit the measuring radiation. According to one embodiment in this context substantially totally means at least 90%, according to a further embodiment at least 99%, in particular at least 99.9% or at least 99.99%. After this the irradiated converter elements are in the passive state. According to the invention one waits until the desired fraction, for example maximum $1/100$ or maximum $1/1000$, of all of the converter elements have returned to the active state. At this time the radiation distribution is irradiated and the places of origin of the emitted measuring radiation are determined, as described above.

In a further embodiment according to the invention the radiation converter further comprises scintillator elements which upon irradiation with exposure radiation produced by the projection exposure tool emit intermediate radiation with an intermediate wavelength. The active converter elements convert the intermediate radiation into the measuring radiation. According to one embodiment the scintillator elements are configured to convert EUV radiation into intermediate radiation in the form of visible light. Photoactivatable fluorescence molecules, which are stimulated to fluorescence by the visible light, are then used as converter elements.

As already explained above, the converter elements in one embodiment according to the invention can be formed by fluorescent elements. The wavelength of the radiation distribution determined can be, for example, as also already mentioned above, within the EUV wavelength range with a wavelength of under 100 nm, for example 13.5 nm or 6.8 nm. According to an alternative embodiment the wavelength of the determined radiation distribution is within the UV wavelength range, for example 193 nm or 248 nm.

In a further embodiment according to the invention, in order to record the respective places of origin of the measuring radiation the places of origin are imaged onto a detector by a microscope objective, and the positions of the is images of the places of origin on the detector are determined with an accuracy which is at least one order of magnitude below the extension of the images caused by diffraction. This is preferably implemented by the respective focal points of the Airy discs being determined on the detector with an accuracy which comes well below the extension of the Airy discs.

In a further embodiment according to the invention, in order to determine the respective places of origin of the measuring radiation the places of origin are imaged onto a detector by using an astigmatic microscope objective, and from the shape of the images on the detector an axial position coordinate of the place of origin in relation to the propagation direction of the radiation distribution is determined. In this case the Airy discs have an ellipticity which is indicative of the axial position of the corresponding photoactivatable elements. This makes possible, for example, three-dimensional measurement of the lithographic process window.

In a further embodiment according to the invention the radiation converter comprises a container which contains the converter elements in a liquid solution.

In this embodiment the converter elements can in particular be in the form of the photoactivatable fluorescence molecules known from cell microscopy. In this embodiment the whole measuring process should be carried out so quickly that between the measuring cycles the converter elements move spatially by less than the resolution limit due to diffusion in the liquid solution. According to a further embodiment according to the invention the converter elements are embedded into a transparent matrix which slows down the diffusion. One can consider here e.g. "water glass", i.e. glass-like sodium and potassium silicate, solidified from a molten mass.

In a further embodiment according to the invention the container is permeable to the radiation distribution from one side and permeable to the wavelength-converted radiation from another side. According to one embodiment one side is formed by a SiN membrane (permeable to EUV radiation) or a small quartz glass is plate (permeable to 193 nm radiation), whereas the second side has a small glass plate (permeable to visible light).

In a further embodiment according to the invention the radiation converter has a membrane on which the converter elements are arranged evenly distributed. The converter elements can thus be arranged, for example, in a uniform grid pattern on the membrane. According to one embodiment the converter elements are applied to the membrane as a monolayer of fluorescent latex beads.

In a further embodiment according to the invention the converter elements are arranged at least two-dimensionally substantially uniformly distributed within the radiation converter, in particular the converter elements are arranged at least two-dimensionally uniformly distributed within the radiation converter. Within this context the term "uniformly distributed" should include a statistical uniform distribution, such as for example when arranging the converter elements in a liquid solution, and a uniform distribution, such as for example in the form of a uniform grid. In particular, there is a uniform grid pattern when the grid period varies by 50% or less, in particular by less than 10%.

In a further embodiment according to the invention the radiation converter is introduced into the image plane or the wafer plane of the projection exposure tool for irradiation with the radiation distribution. According to one variant the radiation converter is integrated into the moveable substrate table or into a measuring table of the projection exposure tool.

Furthermore, the aforementioned object is achieved, according to a further aspect of the invention, with a method for the locally resolved measurement of a radiation distribution produced using a lithography mask which comprises: providing a radiation converter having an at least two-dimensional arrangement of converter elements which are respectively configured to convert incoming radiation with respect to its wavelength, irradiating the radiation converter with the radiation distribution produced by the projection exposure tool so that the converter is elements emit wavelength-converted measuring radiation, and determining the radiation distribution from the measuring radiation with a super-resolving accuracy. Super-resolving accuracy is understood to mean an accuracy which exceeds the accuracy of resolution caused by diffraction, in particular by at least one order of magnitude. The resolution caused by diffraction is defined by the size of the Airy disc of an imaged point source of the measuring radiation. According to one embodiment the super-resolving accuracy is understood to be an accuracy of better than 20 nm, preferably better than 10 nm.

Furthermore, the aforementioned object is achieved, according to yet another aspect of the invention, with an apparatus for the locally resolved measurement of a radiation distribution. The apparatus according to the invention comprises: a radiation converter having a substantially uniformly distributed, in particular a uniformly distributed, at least two-dimensional arrangement of individually photoactivatable converter elements which are configured to convert irradiated radiation with respect to its wavelength in the activated state, a radiation source for the photoactivation of individual converter elements of the radiation converter, and an image detection device for detecting a place of origin of the wavelength-converted radiation.

Within this context the term "uniformly distributed" should, as already explained above, include a statistical uniform distribution, such as for example when arranging the converter elements in a liquid solution, and a deterministically uniform distribution, such as for example in the form of a uniform grid pattern.

According to one embodiment the apparatus according to the invention is configured to measure, locally resolved, a radiation distribution produced by a projection exposure tool for microlithography. According to a further embodiment the apparatus is configured to measure, locally resolved, the radiation distribution produced by the lithography mask to be measured in a mask inspection apparatus.

Furthermore, according to a further aspect of the invention, a projection exposure tool for microlithography is provided which comprises: a radiation converter having an at least two-dimensional arrangement of converter elements which can respectively be put in an active state and a passive state and are configured to only convert exposure radiation of the projection exposure tool into a wavelength-converted measuring radiation in the active state. The projection exposure tool further comprises an image detection device for detecting a place of origin of the measuring radiation. Here the projection exposure tool is configured to manipulate the radiation converter such that only a fraction of the converter elements adopts the active state.

Moreover, according to another aspect of the invention, a projection exposure tool for microlithography is provided which comprises a radiation detector with a detection surface. The radiation detector is configured to measure exposure radiation of the projection exposure tool irradiated onto the detection surface with a local resolution of better than 20 nm, in particular better than 10 nm. This is therefore a two-dimensional aerial image detector which, contrary to the previously known scanning aerial image measuring methods, detects the aerial image two-dimensionally. As in the method according to the invention described above, the measurement can well comprise a number of measuring steps. With each measuring step two-dimensional detection of a partial image takes place here. With the radiation detector according to the invention simultaneous signal detection takes place over the whole detection area in relation to which the aerial image is detected with the aforementioned local resolution. In other words, the radiation detector measures the aerial image in parallel, at least two-dimensionally. According to one embodiment the radiation detector is configured as the apparatus described above for the locally resolved measuring of a radiation distribution.

In advantageous embodiments the projection exposure tool according to the invention is configured to implement the measuring method according to the is invention according to the embodiments described above.

Furthermore, according to yet another aspect of the invention, a mask inspection device for inspecting a lithography mask is provided. The mask inspection device according to the invention comprises imaging optics for imaging mask structures into an image plane using inspection radiation, and a radiation converter disposed in the image plane having an at least two-dimensional arrangement of converter elements. The converter elements can be put respectively in an active state and a passive state and are configured to convert inspection radiation of the mask inspection device with respect to its wavelength only in the active state. The mask inspection device further comprises an image detection device for detecting a place of origin of the wavelength-converted radiation. The mask inspection device is configured here to manipulate the radiation converter such that only a fraction of the converter elements adopts the active state. The inspection radiation is preferably radiation with the same wavelength as the radiation which is provided to expose the lithography mask in a projection exposure tool. Depending on the mask type the inspection radiation can therefore comprise, for example, 193 nm radiation or be in the EUV wavelength range.

The described embodiment according to the invention of a mask inspection device makes it possible, as described in detail below, to provide the imaging optics with a numerical aperture on the image side which corresponds to the numerical aperture of the projection objective which is used in a projection exposure tool when imaging the mask structures onto a wafer. According to one advantageous embodiment the imaging optics have a numerical aperture of at least 0.8 on the image side.

Preferably the mask inspection device for inspecting a lithography mask has the apparatus described above for the locally resolved measurement of a radiation distribution in an embodiment according to the invention.

The features specified in relation to the embodiments of the method according to is the invention listed above can correspondingly be applied to the apparatus according to the invention, the projection exposure tool according to the invention and the mask inspection device according to the invention. Conversely, the features specified in relation to the embodiments of the apparatus, projection exposure tool or mask inspection device according to the invention listed above can correspondingly be applied to the method according to the invention.

BRIEF DESCRIPTION OF THE DRAWINGS

The above and further advantageous features of the invention are illustrated in the detailed description given below of exemplary embodiments according to the invention with reference to the attached diagrammatic drawings. These show as follows.

DETAILED DESCRIPTION OF EXEMPLARY EMBODIMENTS

In the exemplary embodiments described below elements which are functionally or structurally similar to one another are provided as far as possible with the same or similar reference numbers. Therefore, in order to understand the features of the individual elements of a specific exemplary embodiment, one should refer to the description of other exemplary embodiments or to the general description of the invention.

Figure 1:
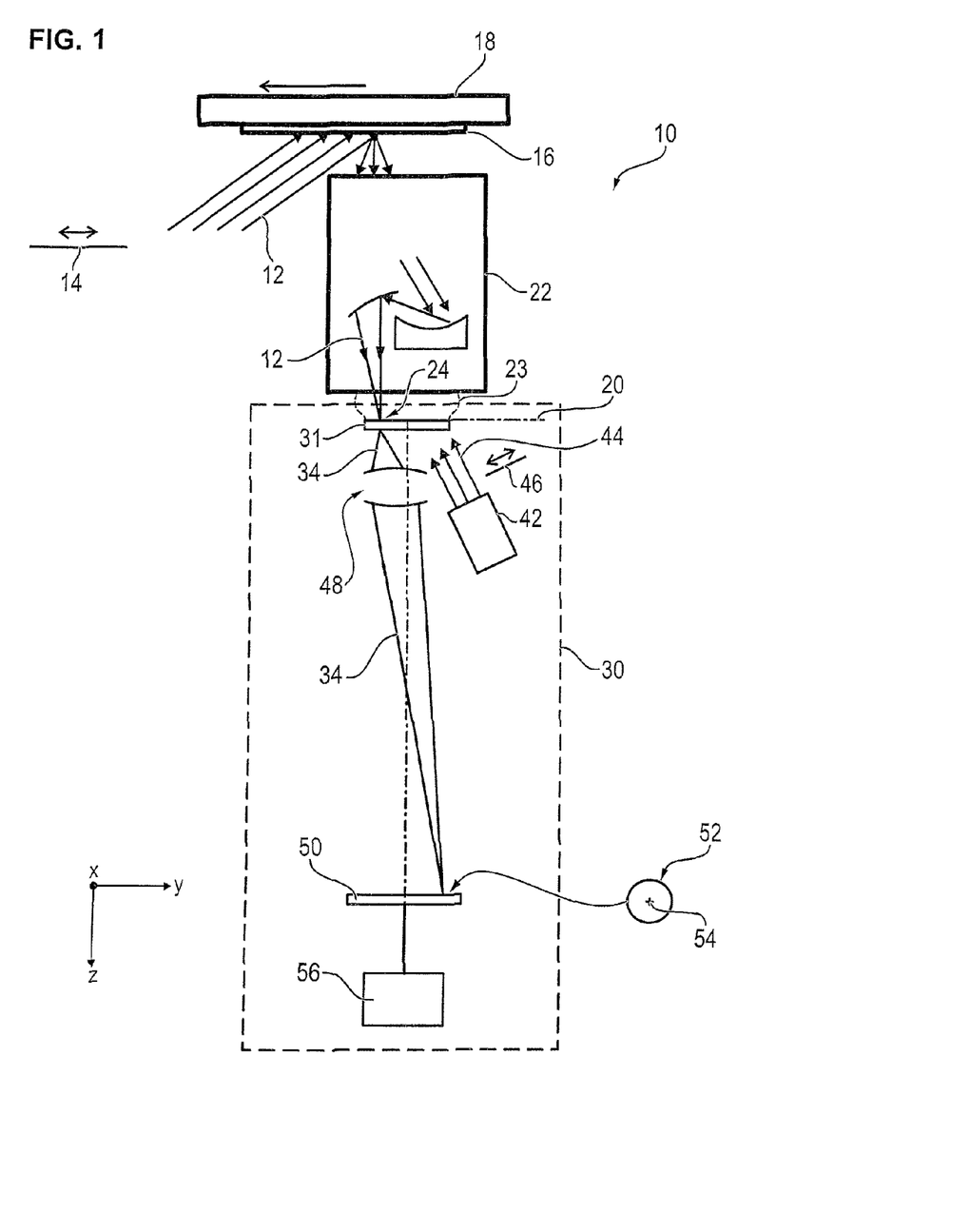
FIG. 1 a projection exposure tool for microlithography with a first embodiment of an apparatus according to the invention for the locally resolved measurement of a radiation distribution in an image plane of the projection exposure tool, FIG. 2 a sectional view of a radiation converter contained in the apparatus according to FIG. 1, FIG. 3 a top view of the radiation converter according to FIG. 1 in a first embodiment with a plurality of converter elements, FIG. 4 the radiation converter according to FIG. 3 with an exemplary illustration of activated converter elements, FIG. 5 a top view of the radiation converter according to FIG. 1 in a is second embodiment, FIG. 6 a top view of the radiation converter according to FIG. 1 in a third embodiment, FIG. 7 the projection exposure tool for microlithography according to FIG. 1 with a second embodiment of an apparatus according to the invention for the locally resolved measurement of the radiation distribution in the image plane, and FIG. 8 a mask inspection device for inspecting a lithography mask with an apparatus according to the invention for the locally resolved measurement of a radiation distribution produced by imaging the lithography mask.

In order to facilitate the description of the projection exposure tool a Cartesian xyz coordinate system is specified in the drawings from which one can gather the respective relative position of the components shown in the figures. In FIG. 1 the x direction runs perpendicularly to the plane of the drawing, the y direction to the right and the z direction downwards.

FIG. 1 shows a diagrammatic sectional view of a projection exposure tool 10 for microlithography in which an apparatus 30 is integrated into an embodiment according to the invention. The apparatus 30 is configured to measure, locally resolved, a radiation distribution 24 produced by the projection exposure tool 10 in a substrate plane 20, also called a wafer plane or image plane. This type of radiation distribution 24 is often also called an aerial image of the projection exposure tool 10, this designation being used both when the radiation distribution, as for example with an exposure wavelength of 193 nm, is actually present in air or a liquid, such as e.g. water, and in the case in which the radiation distribution is present in a vacuum, as when using EUV radiation.

The projection exposure tool 10 comprises a radiation source, not shown by the drawing in FIG. 1, and an illumination system for producing an exposure radiation 12. The exposure radiation 12 can be so-called DUV radiation, i.e. radiation in the deep UV wavelength range with a wavelength of e.g. 248 nm or 193 nm. Alternatively, it can also be EUV radiation (extreme ultraviolet radiation) with a wavelength of <100 nm, in particular a wavelength of approximately 13.5 nm or approximately 6.8 nm. The exposure radiation 12 can be switched on and off. This can be implemented, for example, with an aperture 14 in the optical path of the exposure radiation 12. Alternatively, the radiation source can itself also be designed to be switchable.

The exposure radiation 12 strikes a lithography mask 16 with structures to be imaged arranged over the latter. As shown by FIG. 1, the exposure radiation 12 can be reflected on the lithography mask 16 here, as is often the case when using EUV radiation. Alternatively, the lithography mask 16 can also be in the form of a transmission mask. In this case the exposure radiation 12 passes through the mask. The lithography mask 16 is held by a moveable mask table 18. When imaging the structures of the lithography mask 16 the mask table 18 is moved continuously in the y direction, as is normal with the step and scan projection exposure tools known to the person skilled in the art.

The imaging of the mask structures into the substrate plane 20 takes place with a projection objective 22 which is configured in accordance with the design of the projection objective or in accordance with the exposure wavelength from transmission lenses and/or mirrors. The apparatus 30 according to the invention for the locally resolved measurement of the radiation distribution 24 in the embodiment shown in FIG. 1 comprises a radiation converter 31 having a two-dimensional detection surface, an activation radiation source 42, magnifying imaging optics 48, a locally resolving radiation detector 50 and an evaluation unit 56. The activation radiation source 42 is either switchable or is provided with a moveable aperture 46 for interrupting the activation radiation 44. Dependent upon the exposure wavelength an immersion liquid can be disposed between the projection objective 22 and the radiation converter 31, as indicated by a broken line in FIG. 1.

Figure 2:
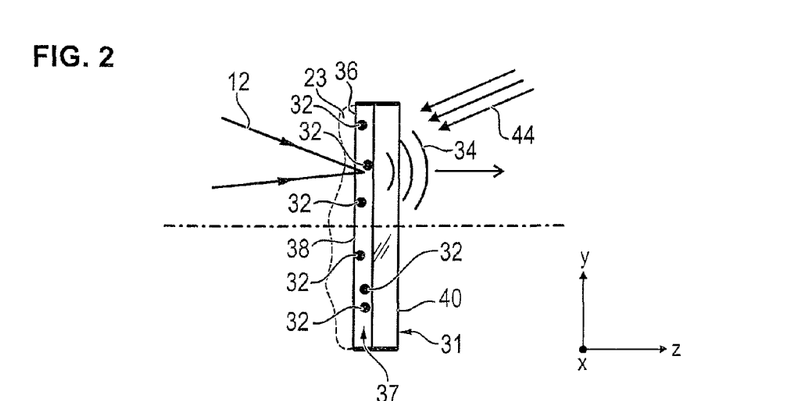

In FIG. 2 the radiation converter 31 is shown in detail in a first embodiment. In this embodiment the radiation converter comprises a container 36 which is in the form of a flat box. On its side facing the projection objective 22 the container 36 comprises a layer 38 permeable to exposure radiation. When using 193 nm light as exposure radiation 12 the layer 38 can be made of a glass plate, and for EUV radiation it can be produced for example from a SiN membrane. When using an immersion liquid 23 the refractive index of the layer 38 permeable to exposure radiation is preferably matched to the refractive index of the immersion liquid. The container 36 is filled with a liquid solution 37. Converter elements for converting the incoming exposure radiation 24 into a wavelength-converted measuring radiation 34 are contained in the liquid solution.

In the present embodiment the converter elements 32 are formed by photoactivatable fluorescence dyes. These fluorescence dyes are known from super-resolving fluorescence microscopy in cell biology. Table 1 below gives an overview of the properties of some organic fluorophores suitable as converter elements 32. These are described in greater detail in the article by Bates M. et al., "Multicolor superresolution imaging with photo-switchable fluorescent probes", Science 2007, 317: 1749-1753. Further possible fluorophores are listed in the article by Bates M. et al., "Super-resolution microscopy by nanoscale localization of photo-switchable fluorescent probes", Current Opinion in Chemical Biology 2008, 12: 505-514, in particular in Table 1 of this document, and are incorporated into the disclosure of this application by explicit reference.

TABLE 1

| Organic fluorophores | Activation wavelength | Absorption maximum - after activation | Emission maximum - after activation |
|---|---|---|---|
| Cy5 | 350-570 nm | 649 nm | 670 nm |
| Cy5.5 | 350-570 nm | 675 nm | 694 nm |
| Cy7 | 350-570 nm | 747 nm | 776 nm |
| Alexa Fluor 647 | 350-570 nm | 650 nm | 665 nm |

By irradiating with an activation radiation 44 the aforementioned fluorophores can be put in an active state in which the latter have fluorescent properties. When using the fluorophores listed in Table 1 above, activation radiation 44 is required which has a wavelength of between 350 nm and 570 nm. After activation has taken place the fluorophores convert irradiated light 12 into fluorescence light acting as measuring radiation 34 in the visible wavelength range.

The fluorophores listed in Table 1 respectively have an absorption maximum for the irradiated light which is above 600 nm. However, it should be possible to stimulate these fluorophores with sufficient effectiveness, even with light with a wavelength of 248 nm or 193 nm. Therefore the aforementioned fluorophores are suitable for analysis of the exposure radiation 12 in the DUV wavelength range. Further fluorophores known to the person skilled in the art, which respond to light of the DUV or the EUV wavelength range, can be used as converter elements 32.

Figure 3:
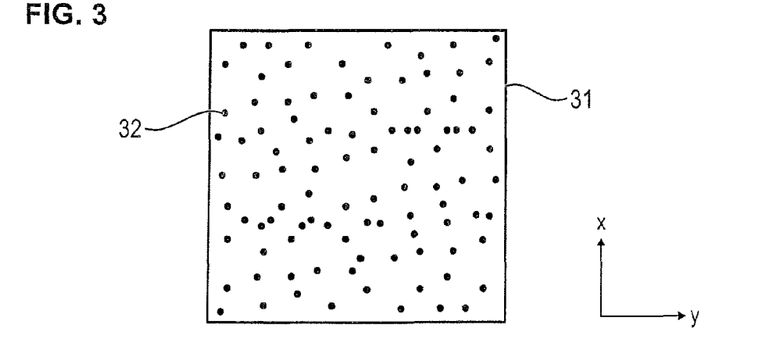
Figure 4:
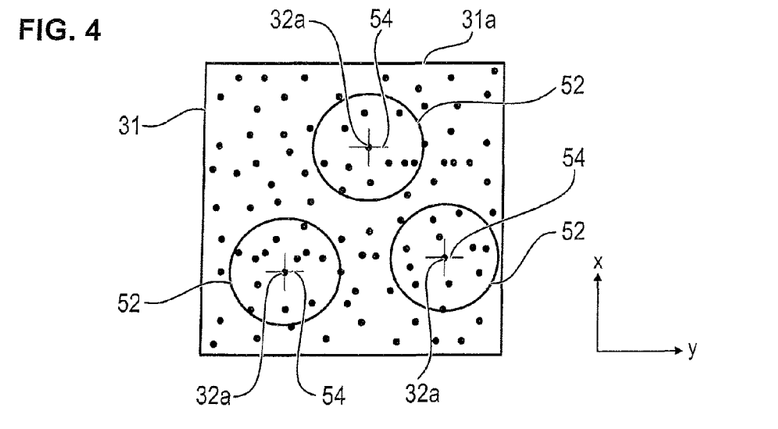

FIG. 3 shows the radiation converter 31 in the embodiment according to FIG. 2 in a is top view from the viewpoint of the incoming exposure radiation 12. The converter elements 32 are statistically uniformly distributed in the plane shown. When implementing the measuring method according to the invention the exposure radiation 12 is first of all interrupted and the activation radiation 44 is irradiated onto the radiation converter 31. Here the intensity and irradiation duration of the activation radiation 44 is chosen such that only a small fraction of the converter elements 32 is activated, i.e. they pass into the state in which they have a fluorescent effect. In FIG. 4 the activated converter elements are identified, for example, by reference number 32a. The number of activated converter elements 32a can be, for example, less than 1/100, in particular less than 1/1000 of the converter elements 32 present.

The exposure radiation 12 is then switched on so that the radiation distribution 24 in the substrate plane 20 stimulates the few activated converter elements 32a to emit the wavelength-converted measuring radiation 34 in the form of fluorescence light. As can further be seen from FIG. 1 the places of origin of the measuring radiation 34 are imaged using magnifying imaging optics 48 onto a locally resolving radiation detector 50 in the form of a CCD camera. Each of the radiation converters 32 emitting measuring radiation produces on the radiation detector 50 an extended radiation distribution in the form of a so-called Airy disc 52. The center of the Airy disc 52 corresponds to the place of origin of the measuring radiation 34 producing the respective Airy disc 52.

As shown in FIG. 4, the place of origin 54 corresponds with the exact position of the activated converter element 32a emitting the respective measuring radiation 34. Since, however, only a small fraction of the converter elements 32 provided in the preceding procedural step was activated, the individual Airy discs produced on the radiation detector 50 typically do not overlap. This makes it possible to precisely determine the center point of the Airy discs, and thus the respective places of origin 54 from the Airy discs 52 recorded. This takes place using an evaluation unit 56.

The procedure just described, namely the activation of a few converter elements 32, irradiation of the radiation distribution 24 and determining the places of origin 54 of the measuring radiation 34 emitted is repeated until a sufficient number of places of origin 54 have been recorded in order to be able to put together the whole radiation distribution 24 with the desired accuracy by combining the recorded places of origin 54.

The time required to perform the locally resolved measurement of the radiation distribution 24 in the substrate plate 20 of the projection exposure tool 10 in an area of about 10 µm×10 µm is on the order of about one minute. This time includes repeating of the described procedure often enough to obtain the whole radiation distribution with the desired accuracy.

The principle of putting together the partial images is known in principle from high resolution microscopy in cell biology under the name STORM (Stochastic Optical Reconstruction Microscopy), see e.g. WO 2008/091296 A2, PAL-M, see e.g. WO 2006/127692 A1 or GSDIM, see e.g. US 2009/0134342 A1. With these methods components of cells are marked with photoactivatable fluorescence dyes and then, by successive activation of the fluorescence dyes, respective illumination and recording of the fluorescence radiation, the distribution of the photoactivatable fluorescence dyes is measured. A significant difference between the measuring according to the invention of the lithography aerial image and the known super-resolving fluorescence microscopy is that the converter elements 32 in the method according to the invention are uniformly distributed, in particular statistically uniformly distributed, over the irradiated area of the converter element 32, see e.g. the exemplary embodiment according to FIG. 3. In contrast to this, with high resolution fluorescence microscopy the fluorescence dyes mark cell structures to be examined, and so are disposed localized in specific structures.

The uniform distribution of the converter elements makes it possible to measure, locally resolved, a radiation distribution in the form of an aerial image from lithography.

The container 36 of the radiation converter 31 according to FIG. 2 has on the side opposite the layer 38 a layer 40 permeable to measuring radiation, e.g. in the form of a glass plate. The recording of the Airy discs 52 using the radiation detector 50 takes place so quickly that the converter elements 32 only move slightly in the aqueous solution during the recording time, but in any case less than the resolution limit.

According to one embodiment according to the invention the imaging optics 48 are deliberately designed to be slightly astigmatic. The form of the Airy discs 52 is therefore slightly elliptical, but with an unchanged focal point position. This ellipticity is indicative of the position of the converter element 32 emitting the measuring radiation 34 in the z direction. By evaluating the elliptical properties of the Airy discs recorded it becomes possible to resolve the radiation distribution 24 three-dimensionally. This makes it possible to determine the so-called process window in lithography without exposing wafers.

The process window in lithography specifies in particular the axial extension of the aerial image and the resulting depth of focus. This substantially determines the accuracy with which the resist layer must be introduced into the aerial image, and so affects the technical requirements of the substrate table and the projection exposure tool as a whole. In order to implement the process window measuring technique the thickness of the radiation converter 31 is configured in the z direction such that the liquid solution 37 with the converter elements 32 extends over an area in the z direction which is larger than the depth of focus sought for the imaging of the desired mask structures. Alternatively, the radiation converter 31 can be moved together with the localization optics, i.e. the whole measuring apparatus 30, in the z direction.

Figure 5:
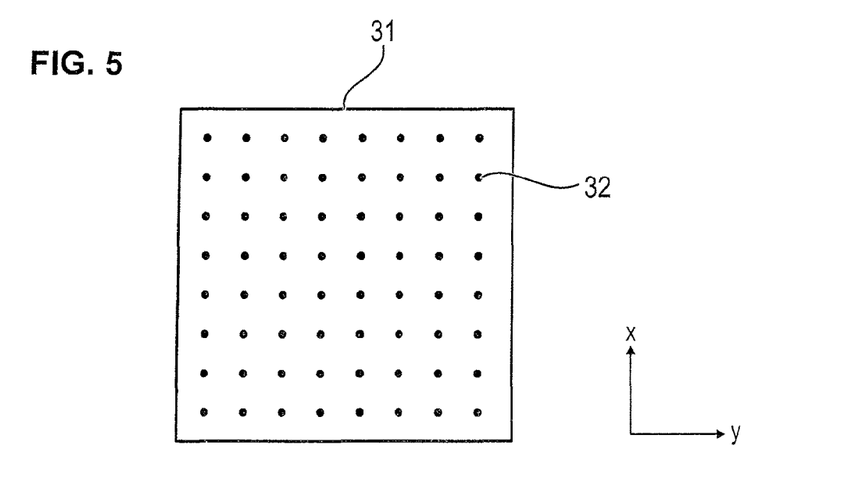

According to a further embodiment according to the invention the converter elements 32 according to FIG. 3 can also be fixed in a transparent matrix, such as for example in water glass, instead of in an aqueous solution. Moreover, the converter elements 32 can also, as shown in FIG. 5, be arranged in a uniform grid is pattern. This can be implemented, for example, by applying a monolayer of fluorescent latex beads to the layer 38 permeable to exposure radiation.

Figure 6:
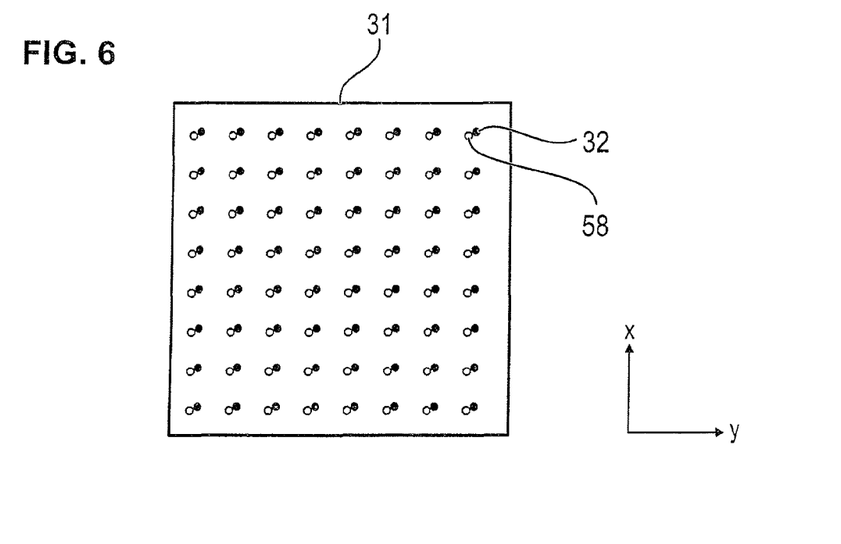

FIG. 6 shows a further embodiment of the radiation converter 31 which is configured especially for measuring the radiation distribution 24 of EUV radiation. In this embodiment the converter elements 32 in the form of a photoactivatable fluorescence dye, for example a dye from Table 1, are arranged in a fixed grid pattern, as in the embodiment according to FIG. 5. The radiation converter 31 further comprises a grid of scintillator elements 58 which are configured to convert the exposure radiation 12 in the EUV wavelength range into an intermediate radiation in the visible wavelength range. The grid of the scintillator elements 58 has element spacings comparable to the grid of the converter elements 32.

Product P43 made by the company Proxitronic Detector Systems, for example, can be considered as a scintillator element. This product has the following composition: $Gd_2O_2S$:Tb. The emission radiation emitted by this product is in the wavelength range of 360 nm to 680 nm and so is suitable for stimulating for example the Cy5 fluorophores and Alexa Fluor 647 according to Table 1 above.

When implementing the method according to the invention using the radiation converter 31 from FIG. 6, with each exposure step all of the scintillator elements 58 are stimulated to emit the radiation in the visible range, whereupon the respectively activated converter elements 32 then emit the measuring radiation 34 in the form of photoactivatable fluorophores with a characteristic wavelength. It may be advantageous here to position in front of the radiation detector 50 a wavelength filter which blocks out radiation with wavelengths below the wavelength of the measuring radiation 34 emitted by the fluorescence dye. In particular the Cy5.5 fluorophore from Table 1 can be considered as a converter element 32 because the latter has an emission maximum above the wavelength range of the radiation emitted by the aforementioned scintillator elements 58. Alternatively, an appropriate scintillator can itself optionally be considered as a converter element 32.

Figure 7:
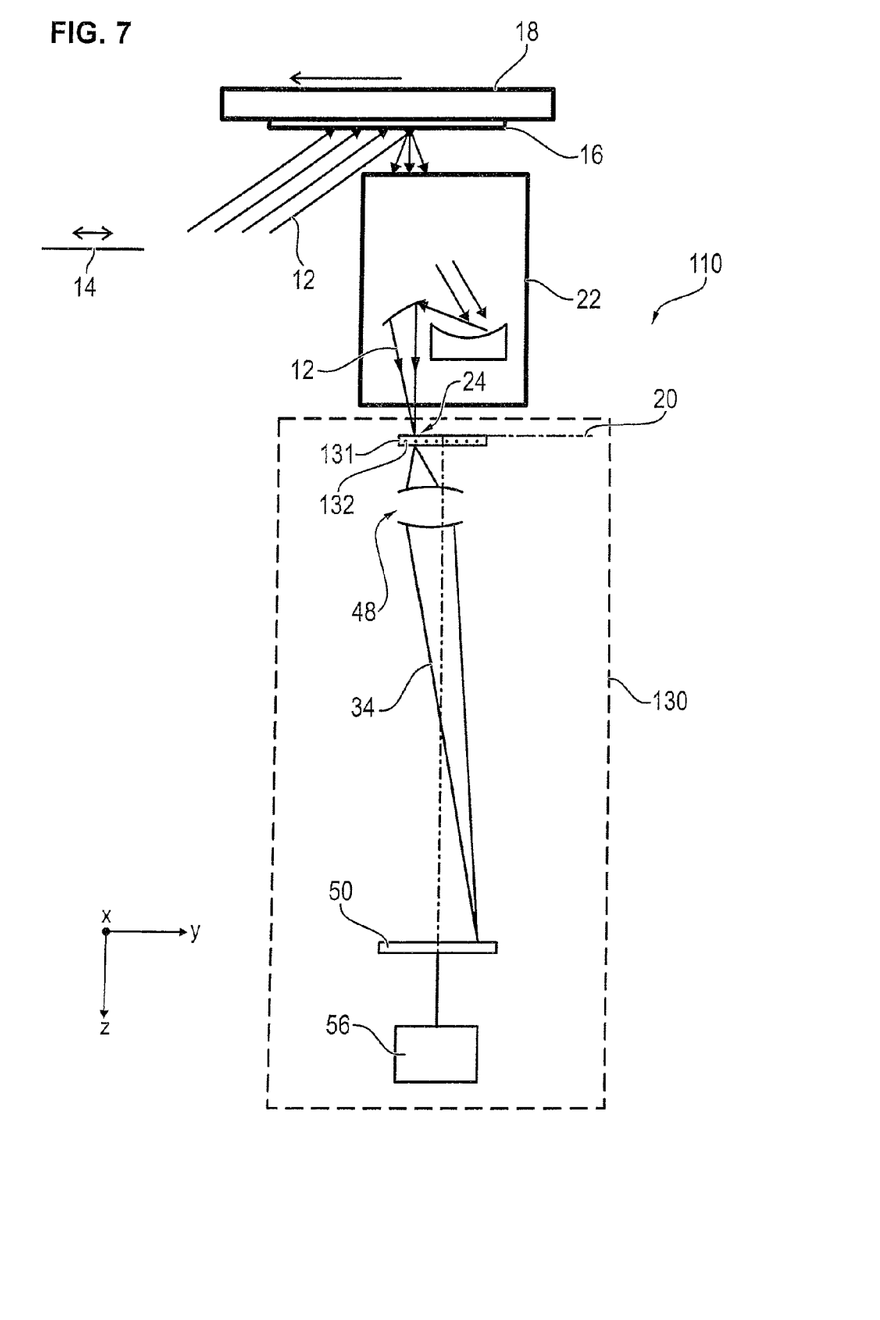

FIG. 7 shows a further embodiment 110 according to the invention of a projection exposure tool for microlithography having an apparatus 130 for the locally resolved measurement of radiation distribution in the substrate plane 20. The projection exposure tool 110 only differs from the projection exposure tool 10 in the embodiment of the apparatus for the locally resolved measurement of radiation distribution which has no activation radiation source 42 in the embodiment 130 according to FIG. 7. Furthermore, the radiation converter in the embodiment 131 according to FIG. 7 is provided with a different type of converter element 132. The converter elements 132 are configured such that directly after emitting the wavelength-converted measuring radiation 34 they pass temporarily into a passive state in which the converter elements 132 do not convert incoming exposure radiation 12 in respect of its wavelength. In other words, after emitting the measuring radiation 34, such as for example fluorescence radiation, the converter elements 132 have a dead time. The spatial arrangement of the converter elements 132 in the radiation converter can take place in a configuration described above with regard to FIGS. 3 to 5.

According to the invention, when operating the projection exposure tool 110 according to FIG. 7 the radiation converter 131 is now irradiated two-dimensionally with exposure radiation 24 such that substantially all of the converter elements 132 are stimulated to emit the wavelength-converted measuring radiation 34, in particular to fluorescence. This is implemented using a so-called flood exposure with which the whole area in the substrate plane 20 to be exposed is irradiated uniformly. The flood exposure should preferably be configured such that at least 99%, preferably at least 99.9% or at least 99.99% of the converter elements 132 emit the measuring radiation 34.

After implementing the flood exposure individual converter elements 132 pass back little by little into the active state in which they can be stimulated again to emit the measuring radiation 34. This falling back into the active state is a statistical process. According to the invention, after implementing the flood is exposure one waits for a period of time over which a small fraction of the converter elements 132 have returned to the active state. This portion should correspond approximately to the fraction of the converter elements activated through the activation radiation source 42 according to FIG. 1, and so can be e.g. approximately 1/1000.

Directly after the aforementioned period of time has expired, the radiation distribution 24 is then produced in the substrate plane 20 by the lithography mask 16, and as already described with regard to FIG. 1 the places of origin 54 of the elements 132 emitting the measuring radiation 34 is determined. The aforementioned procedural steps are repeated several times in the same way as in the method according to FIG. 1, and the radiation distribution 24 is then reconstructed with a high resolution from the places of origin recorded. The materials listed in the document by Mike Heilemann et al., "Super-resolution imaging with small organic fluorophores", Applied Chemistry International Edition, 1 Sep. 2009, vol. 48, No. 37, pages 6903-6908 in relation to the dSTORM method can, for example, be considered as substances which are suitable as converter elements 132 according to the embodiment according to FIG. 7.

Therefore, for example the substances Alexa Fluor 488 (absorption maximum 488 nm), ATTO520, Alexa Fluor (absorption maximum 514 nm), ATTO565, Alexa Fluor 568 (respective absorption maximum 468 mm), ATTO655 and ATTO700 (respective absorption maximum 647 mm) listed in the document can be used.

As do also the molecules from Table 1, these substances have absorption maxima for the irradiated light above the lithography wavelengths in the DUV and EUV. However, it should also be possible to stimulate these substances with sufficient effectiveness with light with a wavelength of 248 nm or 193 nm. Further fluorophores known to the person skilled in the art with the properties described above, which respond to light in the DUV or the EUV wavelength range, can also be used as converter elements 32.

Figure 8:
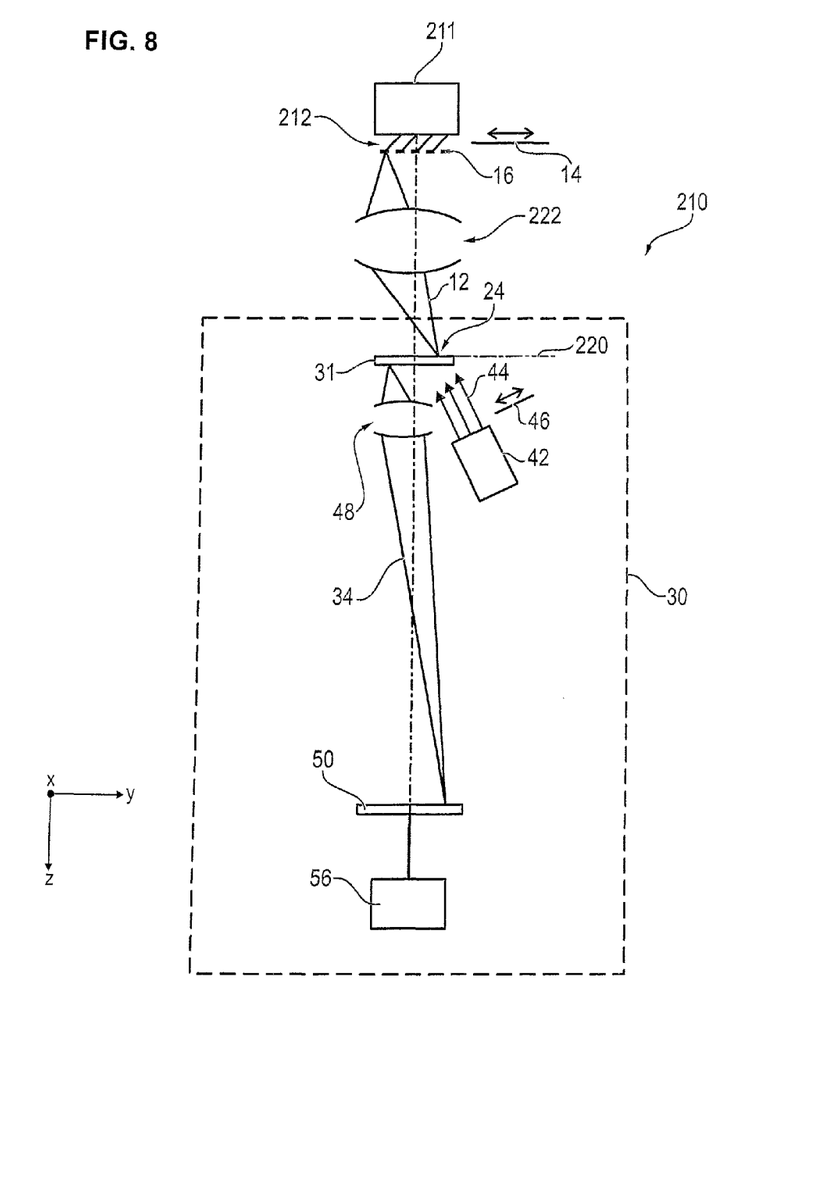

FIG. 8 shows a mask inspection device 210 for inspecting a lithography mask 16. is This type of mask inspection device 210 serves to measure the aerial image of the lithography mask 16 outside of a projection exposure tool in order to recognize writing errors of the mask. The mask inspection device 210 comprises an illumination system 211 for producing inspection radiation 212 of the wavelength for which the lithography mask 16 is configured when used in a projection exposure tool.

Therefore the inspection radiation 212 can be in the DUV wavelength range, e.g. 248 nm or 193 nm, or also in the EUV wavelength range. The lithography mask 16 is then imaged into an image plane 220 with imaging optics 222. Here the radiation converter 31 is disposed in one of the embodiments described above. This is part of the apparatus 30 for the locally resolved measurement of the radiation distribution 24 which corresponds to the apparatus 30 according to FIG. 1. Alternatively, the apparatus 130 according to FIG. 7 can also be disposed beneath the imaging optics 222.

With the apparatus 30 or 130 it is now possible, as described above, to measure the spatial distribution of the radiation 24 with greatly improved accuracy. The aerial image can be measured with a high numerical aperture. It thus becomes possible to provide the imaging optics 222 with the same numerical aperture on the image side as the projection objective of the projection exposure tool in which the lithography mask is to be used. This reduces measuring inaccuracies. Customarily the imaging optics of a mask inspection device have a substantially smaller numerical aperture on the image side since due to the high measuring accuracy required for the aerial image 24 the imaging optics are designed as magnifying imaging optics. Contrary to this, projection objectives in an exposure tool are reducing optics.

Upon the basis of the Lagrange invariant the use of reducing optics leads to a large numerical aperture on the image side. The result of this is that the aerial image produced with a conventional mask inspection device differs from the aerial image in the projection exposure tool. These differences must customarily be considered mathematically, and this leads to inaccuracies.

The time required to perform the locally resolved measurement of the radiation distribution 24 in the image plane 220 of the mask inspection device 210 in an area of about 10 μm×10 μm is on the order of about one minute.

In the following the differences between the mode of operation of the aerial image measuring method in an embodiment according to the invention and the mode of operation of conventional aerial image measuring methods are described. As already mentioned at the start, with the conventional aerial image measuring methods a distinction is made between imaging and scanning methods. With imaging aerial image measuring methods two-dimensional image recording is implemented, a single image recording already providing the aerial image, whereas with the scanning aerial image measuring technique point by point image recording is implemented, and only a very large number of point by point image recordings brought together produce the aerial image.

With the described embodiment of the measuring method according to the invention a plurality of partial images are recorded. Here each of the partial images covers the whole two-dimensional detection area, only a statistical selection of pixel elements respectively being active in the detection area, however, and so the respective partial image having statistically distributed points. According to the invention the partial images are added together, and this produces the aerial image. In comparison to the imaging method with which a single recorded image already produces the aerial image, and the scanning method with which very many point by point recorded images are brought together to form the aerial image, with the method according to the invention an average number of partial images in combination provides the aerial image.

Both with the imaging and with the scanning method the image pixels, i.e. the locations of the two-dimensional elements where the aerial image is measured, is are established, i.e. determined, in advance. In contrast, with the embodiment according to the invention the locations of the points at which the aerial image is measured is different from partial image to partial image and respectively chosen statistically. In other words, with the conventional methods the measurement is implemented deterministically, whereas the measurement in the embodiment according to the invention is statistical.

With the imaging aerial image measuring technique the aerial image resolution is determined by the number and size of the two-dimensional elements, and with the scanning aerial image measuring technique by the free opening of the point detector. However, with the embodiment according to the invention the aerial image resolution is given by the localization accuracy of individual fluorescent markers. With the imaging method the localization of an observed structure is implemented by localization of its image on the camera, with the scanning method by knowledge of the detector position. With the embodiment according to the invention, however, an observed structure is localized in particular by determining the focal point of an Airy disc on a camera. Finally, with the embodiment according to the invention a wavelength conversion takes place, but not with the aforementioned conventional aerial image measuring method.

With imaging measuring methods the resolution limit is the Abbe imaging limit, and so approximately 200 nm. Thus, through a scanning measuring method a higher resolution can be achieved, limited by the opening of near field probes which is often approx. 50 nm. With the measuring method according to the invention, however, the resolution limit can fall to the order of magnitude of the molecule diameter, and so to approximately 10-20 nm.

The above description of various embodiments has been given by way of example. From the disclosure given, those skilled in the art will not only understand the present invention and its attendant advantages, but will also find apparent various changes and modifications to the structures and methods disclosed. It is sought, therefore, to cover all such changes and modifications as fall within the spirit and scope of the invention, as defined by the appended claims, and equivalents thereof.

The invention claimed is:

1. A projection exposure tool for microlithography, comprising a radiation detector with a detection surface, configured to perform a radiation measurement simultaneously at plural locations of the detection surface and to measure a distribution of exposure radiation of the projection exposure tool irradiated onto the detection surface with a local resolution resolving structures smaller than 20 nm.

2. The projection exposure tool according to claim 1, wherein the radiation detector is configured to measure the exposure radiation with a local resolution of resolving structures smaller than 10 nm.

3. The projection exposure tool according to claim 1, wherein the wavelength of the measured radiation is within the extreme-ultraviolet wavelength range.

4. The projection exposure tool according to claim 1, wherein the wavelength of the measured radiation is within the ultraviolet wavelength range.

5. The projection exposure tool according to claim 1, wherein the simultaneous radiation measurement extends over an entirety of a used portion of the detection surface.

6. A projection exposure tool for microlithography, comprising:
a radiation detector with a detection surface configured to measure a distribution of exposure radiation of the projection exposure tool irradiated onto the detection surface with a local resolution resolving structures smaller than 20 nm,
wherein the radiation detector comprises an apparatus for the locally resolved measurement of a radiation distribution, comprising:
a radiation converter with a substantially uniformly distributed at least two-dimensional arrangement of individually photoactivatable converter elements which are configured to convert irradiated radiation with respect to wavelength in an activated state,
a radiation source arranged to photoactivate individual converter elements of the radiation converter, and
an image detection device configured to detect a place of origin of the wavelength-converted radiation.

7. The projection exposure tool according to claim 6, wherein the converter elements are statistically uniformly distributed in at least two dimensions.

8. The projection exposure tool according to claim 6, wherein the converter elements are arranged in at least two dimensions uniformly distributed.

9. A projection exposure tool for microlithography comprising:
a radiation detector with a detection surface configured to measure a distribution of exposure radiation of the projection exposure tool irradiated onto the detection surface with a local resolution resolving structures smaller than 20 nm, wherein the radiation detector comprises:
a radiation converter having an at least two-dimensional arrangement of converter elements which have alternatively an active state and a passive state, and are configured to convert exposure radiation of the projection exposure tool into a wavelength-converted measuring radiation only in the active state,
an image detection device configured to detect a place of origin of the measuring radiation, and
a further component configured to manipulate the radiation converter such that only a fraction of the converter elements adopts the active state at any given time.

10. The projection exposure tool according to claim 9, wherein the converter elements are configured such that directly after emitting the wavelength-converted measuring radiation the converter elements pass temporarily into the passive state in which the converter elements do not convert incoming radiation with respect to their wavelength, said manipulation of the radiation converter is implemented by the radiation converter initially being irradiated with radiation of such an intensity that substantially all of the converter elements are stimulated to emit the wavelength-converted measuring radiation, and are thereby temporarily put in the passive state, and the radiation distribution is irradiated onto the radiation converter at a time when only a fraction of the converter elements has returned to the active state.

11. The projection exposure tool according to claim 9, wherein the radiation converter further comprises scintillator elements which upon irradiation with exposure radiation produced by the projection exposure tool emit intermediate radiation with an intermediate wavelength, and the active converter elements convert the intermediate radiation into the measuring radiation.

12. The projection exposure tool according to claim 9, wherein the converter elements are formed by fluorescent elements.

13. The projection exposure tool according to claim 9, wherein the converter elements are arranged at least two-dimensionally substantially uniformly distributed within the radiation converter.

14. The projection exposure tool according to claim 9, wherein the radiation converter has a membrane on which the converter elements are arranged evenly distributed.

15. A projection exposure tool for microlithography, comprising:
a radiation detector with a detection surface configured to measure a distribution of exposure radiation of the projection exposure tool irradiated onto the detection surface with a local resolution resolving structures smaller than 20 nm,
wherein the radiation detector comprises a radiation converter with individually photoactivatable converter elements provided in a container which contains the converter elements in a liquid solution.

16. The projection exposure tool according to claim 15, wherein the container is permeable to the radiation from one side and permeable to the wavelength-converted radiation from another side.

17. A projection exposure tool for microlithography, comprising a radiation detector with a detection surface, configured to measure exposure radiation of the projection exposure tool irradiated onto the detection surface with a local resolution resolving structures smaller than 20 nm, wherein the radiation detector comprises converter elements configured to convert the exposure radiation into a wavelength-converted measuring radiation.

* * * * *

UNITED STATES PATENT AND TRADEMARK OFFICE
CERTIFICATE OF CORRECTION

| | |
|---|---|
| PATENT NO. | : 8,822,942 B2 |
| APPLICATION NO. | : 13/973078 |
| DATED | : September 2, 2014 |
| INVENTOR(S) | : Rolf Freimann |

It is certified that error appears in the above-identified patent and that said Letters Patent is hereby corrected as shown below:

On the Title Page, Item (57):

In the Abstract:

Page 1; Column 2; Line 14; change "is measuring" to -- measuring --.

In the Specification:

Column 1; Line 20; change "is radiation" to -- radiation --.

Column 1; Line 57; change "is object" to -- object --.

Column 2; Line 27; change "is radiation" to -- radiation --.

Column 2; Line 64; change "is present" to -- present --.

Column 3; Line 35; change "is Mark" to -- Mark --.

Column 4; Line 41; change "is are" to -- are --.

Column 5; Line 10; change "is images" to -- images --.

Column 5; Line 48; change "is plate" to -- plate --.

Column 6; Line 18; change "is elements" to -- elements --.

Column 7; Line 25; change "is invention" to -- invention --.

Signed and Sealed this
Twenty-ninth Day of September, 2015

Michelle K. Lee
*Director of the United States Patent and Trademark Office*

CERTIFICATE OF CORRECTION (continued)
U.S. Pat. No. 8,822,942 B2

Column 7; Line 63; change "is the" to -- the --.

Column 8; Line 26; change "is second" to -- second --.

Column 9; Line 64; change "is al.," to -- al., --.

Column 10; Line 36; change "is top" to -- top --.

Column 12; Line 14; change "is pattern." to -- pattern. --.

Column 13; Line 24; change "is exposure" to -- exposure --.

Column 13; Line 63; change "is This" to -- This --.

Column 15; Line 3; change "is are" to -- are --.

In the Claims:

Column 15; Line 57; In Claim 2 change "resolution of" to -- resolution --.